US008022031B2

(12) United States Patent
Hansen et al.

(10) Patent No.: US 8,022,031 B2
(45) Date of Patent: *Sep. 20, 2011

(54) LIQUID COMPOSITION OF FACTOR VII POLYPEPTIDES (75) Inventors: Birthe Lykkegaard Hansen, Vaerlose (DK); Michael Bech Jensen, Allerod (DK); Troels Kornfelt, Virum (DK)

(73) Assignee: Novo Nordisk Health Care A/G, Zurich (CH)

( * ) Notice: Subject to any disclaimer, the term of this patent is extended or adjusted under 35 U.S.C. 154(b) by 443 days.

This patent is subject to a terminal disclaimer.

(21) Appl. No.: 10/602,838

(22) Filed: Jun. 24, 2003

(65) Prior Publication Data

US 2004/0037893 A1  Feb. 26, 2004

Related U.S. Application Data (63) Continuation-in-part of application No. PCT/DK02/00895, filed on Dec. 20, 2002.

(60) Provisional application No. 60/346,888, filed on Jan. 7, 2002.

(30) Foreign Application Priority Data

Dec. 21, 2001 (DK) .................................. 2001 01948

(51) Int. Cl.
*A61K 38/00* (2006.01)
*A61K 38/36* (2006.01)
*C07K 14/00* (2006.01)
*C12N 5/00* (2006.01)

(52) U.S. Cl. .......... 514/1.1; 514/12; 530/384; 435/69.1; 435/69.6; 435/254.1; 435/325

(58) Field of Classification Search .................... None
See application file for complete search history.

(56) References Cited

U.S. PATENT DOCUMENTS

| 115,590 | A | | 6/1871 | Flood et al. | |
|---|---|---|---|---|---|
| 4,297,344 | A | | 10/1981 | Schwinn et al. | 424/101 |
| 4,382,083 | A | | 5/1983 | Thomas | |
| 4,404,132 | A | | 9/1983 | Mitra | |
| 4,495,278 | A | | 1/1985 | Thomas | |
| 4,784,950 | A | | 11/1988 | Hagen et al. | |
| 4,956,386 | A | | 9/1990 | McLoughlin et al. | |
| 5,180,583 | A | | 1/1993 | Hedner | |
| 5,288,629 | A | | 2/1994 | Berkner | |
| 5,399,670 | A | | 3/1995 | Bhattacharya et al. | |
| 5,457,181 | A | | 10/1995 | Michalski et al. | |
| 5,576,291 | A | | 11/1996 | Curtis et al. | |
| 5,649,959 | A | * | 7/1997 | Hannam et al. | 606/213 |
| 5,700,914 | A | | 12/1997 | Jorgensen et al. | |
| 5,750,358 | A | | 5/1998 | Morrissey | |
| 5,770,700 | A | | 6/1998 | Webb et al. | 530/383 |
| 5,804,420 | A | | 9/1998 | Chan et al. | |
| 5,817,788 | A | | 10/1998 | Berkner et al. | |
| 5,824,780 | A | | 10/1998 | Curtis et al. | |
| 5,830,852 | A | * | 11/1998 | Thatcher et al. | 514/3 |
| 5,831,026 | A | | 11/1998 | Almstedt et al. | |
| 5,833,982 | A | | 11/1998 | Berkner et al. | |
| 5,874,408 | A | | 2/1999 | Nayar | |
| 5,925,738 | A | | 7/1999 | Miekka et al. | |
| 5,925,739 | A | | 7/1999 | Spira et al. | |
| 5,962,650 | A | | 10/1999 | Osterberg et al. | |
| 5,993,795 | A | * | 11/1999 | Osawa et al. | 424/74 |
| 6,034,222 | A | | 3/2000 | Fischer et al. | |
| 6,183,743 | B1 | | 2/2001 | Hart et al. | |
| 6,228,620 | B1 | | 5/2001 | Chapman et al. | |
| 6,277,828 | B1 | | 8/2001 | Knepp et al. | |
| 6,310,183 | B1 | | 10/2001 | Johannessen et al. | |
| 6,320,029 | B1 | | 11/2001 | Miekka et al. | |
| 6,461,610 | B1 | | 10/2002 | Kongsbak et al. | |
| 6,586,573 | B1 | | 7/2003 | Besman et al. | |
| 6,586,574 | B1 | | 7/2003 | Hansen | |
| 6,599,724 | B1 | | 7/2003 | Mikaelsson et al. | |
| 6,750,053 | B1 | | 6/2004 | Widrig Opalsky et al. | |
| 6,806,063 | B2 | | 10/2004 | Pedersen et al. | |
| 6,825,323 | B2 | | 11/2004 | Hess | |
| 6,833,352 | B2 | * | 12/2004 | Johannessen et al. | 514/2 |
| 6,858,587 | B2 | | 2/2005 | Sorensen et al. | |
| 6,903,069 | B2 | | 6/2005 | Pingel et al. | |
| 6,908,610 | B1 | | 6/2005 | Sato | |
| 7,015,194 | B2 | | 3/2006 | Kjalke | |
| 7,078,479 | B2 | | 7/2006 | Rojkjaer | |
| 7,125,846 | B2 | | 10/2006 | Rojkjaer | |
| 7,173,000 | B2 | | 2/2007 | Ruf et al. | |
| 2001/0031721 | A1 | | 10/2001 | Webb et al. | 514/2 |

(Continued)

FOREIGN PATENT DOCUMENTS

| AU | 2003/289742 | 7/2007 |
|---|---|---|
| CA | 2304396 | 4/1999 |
| CA | 2315309 | 2/2001 |
| DE | 19853033 | 5/2000 |
| EP | 0052874 | 6/1982 |
| EP | 225160 | 6/1987 |
| EP | 547932 | 6/1993 |
| EP | 770625 | 10/1995 |
| EP | 765669 | 7/1996 |
| EP | 0872487 A3 | 10/1999 |
| EP | 952215 | 10/1999 |
| EP | 1232753 | 8/2002 |
| JP | 62-195335 | 8/1987 |
| JP | 3155797 | 7/1991 |
| JP | 6-504678 | 6/1994 |

(Continued)

OTHER PUBLICATIONS

Laegemiddel Kataloget, pp. 893-894 (2000) (translation), Jul. 19, 2000.

(Continued)

*Primary Examiner* — Julie Ha
(74) *Attorney, Agent, or Firm* — Michael J. Brignati (57) ABSTRACT A liquid aqueous composition comprising (i) a factor VII polypeptide, (ii) an agent suitable for keeping pH in the range of from about 4.0 to about 8.0; (iii) an agent selected from the list of: a calcium salt, a magnesium salt, or a mixture thereof; wherein the concentration of (iii) is at least 15 mM.

22 Claims, 1 Drawing Sheet

U.S. PATENT DOCUMENTS

| | | | |
|---|---|---|---|
| 2002/0110552 | A1 | 8/2002 | Romisch et al. |
| 2002/0115590 | A1 | 8/2002 | Johannessen et al. |
| 2003/0109446 | A1 | 6/2003 | Rojkjaer |
| 2004/0009918 | A1 | 1/2004 | Nedergaard et al. |
| 2004/0037893 | A1 | 2/2004 | Hansen et al. |
| 2004/0043933 | A1 | 3/2004 | Hansen et al. |
| 2005/0266006 | A1 | 12/2005 | Rojkjaer |
| 2006/0009376 | A1 | 1/2006 | Eibl |
| 2006/0013812 | A1 | 1/2006 | Rojkjaer |
| 2006/0063714 | A1 | 3/2006 | Jensen et al. |
| 2006/0160720 | A1 | 7/2006 | Jensen et al. |
| 2007/0049523 | A1* | 3/2007 | Hansen et al. .................. 514/12 |
| 2009/0075895 | A1 | 3/2009 | Nedergaard |
| 2009/0181895 | A1 | 7/2009 | Hansen et al. |
| 2010/0136622 | A1 | 6/2010 | Krarup |

FOREIGN PATENT DOCUMENTS

| | | |
|---|---|---|
| JP | 8-509745 | 10/1996 |
| JP | 11-500408 | 1/1999 |
| JP | 2000-302689 | 10/2000 |
| JP | 2000-513720 | 10/2000 |
| JP | 2001-515460 | 9/2001 |
| WO | 88/00210 | 1/1988 |
| WO | 91/10439 | 7/1991 |
| WO | 92/15686 | 9/1992 |
| WO | 93//00807 | 1/1993 |
| WO | WO 94/05692 | 3/1994 |
| WO | 94/22905 | 10/1994 |
| WO | WO 94/26286 | 11/1994 |
| WO | WO 94/26286 A1 | 11/1994 |
| WO | 94/27631 | 12/1994 |
| WO | 95/28954 | 11/1995 |
| WO | 96/12800 | 5/1996 |
| WO | WO 97/14430 | 4/1997 |
| WO | WO 97/19687 | 6/1997 |
| WO | 97/26909 | 7/1997 |
| WO | WO 97/47651 A1 | 12/1997 |
| WO | WO /9747651 | 12/1997 |
| WO | WO 98/12225 | 3/1998 |
| WO | WO 98/22619 | 5/1998 |
| WO | WO 98/48822 | 11/1998 |
| WO | WO 99/02160 | 1/1999 |
| WO | WO 99/49880 | 10/1999 |
| WO | 99/66031 | 12/1999 |
| WO | WO 00/20835 | 4/2000 |
| WO | 00/48635 | 8/2000 |
| WO | WO 2004/48635 | 8/2000 |
| WO | WO 00/72873 | 12/2000 |
| WO | 01/03726 | 1/2001 |
| WO | 01/12653 | 2/2001 |
| WO | WO 01/17542 | 3/2001 |
| WO | WO 01/17567 | 3/2001 |
| WO | WO 01/17569 | 3/2001 |
| WO | WO 01/58935 | 8/2001 |
| WO | 01/82943 | 11/2001 |
| WO | 01/85198 | 11/2001 |
| WO | WO 01/82943 * | 11/2001 |
| WO | WO 01/83725 | 11/2001 |
| WO | WO 01/85199 | 11/2001 |
| WO | WO 02/17957 | 3/2002 |
| WO | WO 02/22776 | 3/2002 |
| WO | 03/007868 | 1/2003 |
| WO | WO 03/002524 | 1/2003 |
| WO | 03/055511 | 7/2003 |
| WO | 03/055512 | 7/2003 |
| WO | WO 03/055511 | 7/2003 |
| WO | 03/092731 | 11/2003 |
| WO | 2004/000347 | 12/2003 |
| WO | 2004008635 | 1/2004 |
| WO | WO 04/082708 | 9/2004 |
| WO | WO 04/110469 | 12/2004 |

OTHER PUBLICATIONS

Manning et al., Pharmaceutical Research, vol. 6, No. 11, pp. 903-918 (1989).
Cleland et al., Critical Reviews in Therapeutic Drug Carrier Systems, vol. 10, No. 4, pp. 307-377 (1993).
Wang et al., Journal of Parenteral Science and Technology, vol. 42, pp. S2-S26 (1988).
NovoSeven® Coagulation Factor VIIa (Recombinant) Package Insert.
Wang, International Journal of Pharmaceutics, vol. 203, pp. 1-60 (2000).
Cooper, A.J.L., Ann. Rev. Biochem., vol. 52, pp. 187-222 (1983).
Enziklopedia lekarstv. M., RLS-2001, 468; Encyclopedia of drugs, p. 468.
International Search Report dated Oct. 20, 2003.
Porter, C.W. et al., Biochem & Biophysical Research Communications, vol. 122, No. 1, pp. 350-357 (1984).
Wang et al., J. Parenter Sci Technol, vol. 42 (10), pp. 4-26 (1988).
Wells, Biochemistry, vol. 29, pp. 8509-8517 (1990).
Notice of Allowance in U.S. Appl. No. 12/154,088, filed May 20, 2008, by Hansen, sent from the USPTO on Feb. 1, 2010.
Non-final Office Action in U.S. Appl. No. 12/154,088, filed May 20, 2008, by Hansen, sent from the USPTO on Jul. 29, 2009.
Notice of Allowance in U.S. Appl. No. 11/304,427, filed Dec. 15, 2005, by Jensen, sent from the USPTO on Dec. 15, 2009.
Non-final in U.S. Appl. No. 11/304,427, filed Dec. 15, 2005, by Jensen, sent from the USPTO on Feb. 6, 2009.
Final Office Action in U.S. Appl. No. 11/304,427, filed Dec. 15, 2005, by Jensen, sent from the USPTO on May 2, 2008.
Non-final Office Action in U.S. Appl. No. 11/304,427, filed Dec. 15, 2005, by Jensen, sent from the USPTO on Sep. 11, 2007.
Abandonment in U.S. Appl. No. 10/602,340, filed Jun. 23, 2003, by Hansen, sent from the USPTO on Aug. 2, 2006.
Final Office action in U.S. Appl. No. 11/473,387, filed Jun. 21, 2006, by Hansen, sent from the USPTO on Dec. 30, 2009.
Non-final Office action in U.S. Appl. No. 11/473,387, filed Jun. 21, 2006, by Hansen, sent from the USPTO on Jan. 29, 2009.
Non-final Office action in U.S. Appl. No. 11/473,387, filed Jun. 21, 2006, by Hansen, sent from the USPTO on Apr. 8, 2008.
Abandonment in U.S. Appl. No. 10/609,780, filed Jun. 30, 2003, by Jensen, sent from the USPTO on Oct. 27, 2006.
Non-final Office action in U.S. Appl. No. 10/609,780, filed Jun. 30, 2003, by Jensen, sent from the USPTO on Mar. 27, 2006.
Non-final Office action in U.S. Appl. No. 11/526,503, filed Sep. 25, 2006, by Jensen, sent from the USPTO on Jan. 4, 2010.
Non-final Office action in U.S. Appl. No. 11/526,503, filed Sep. 25, 2006, by Jensen, sent from the USPTO on Apr. 6, 2009.
Non-final Office Action in U.S. Appl. No. 11/229,427, filed Sep. 15, 2005, by Jensen, sent from the USPTO on Jun. 25, 2008.
Non-final Office Action in U.S. Appl. No. 11/229,427, filed Sep. 15, 2005, by Jensen, sent from the USPTO on Nov. 21, 2007.
Abandonment in U.S. Appl. No. 10/427,395, filed May 1, 2003, by Nedergaard, sent from the USPTO on Jan. 5, 2009.
Non-final Office Action in U.S. Appl. No. 10/427,395, filed May 1, 2003, by Nedergaard, sent from the USPTO on Jun. 14, 2006.
Non-final Office Action in U.S. Appl. No. 10/427,395, filed May 1, 2003, by Nedergaard, sent from the USPTO on May 20, 2008.
Final Office Action in U.S. Appl. No. 10/427,395, filed May 1, 2003, by Nedergaard, sent from the USPTO on Mar. 19, 2007.
Abandonment in U.S. Appl. No. 11/229,427, filed Sep. 15, 2005, by Jensen, sent from the USPTO on Nov. 9, 2009.
Notice of Allowance in U.S. Appl. No. 11/229,427, filed Sep. 15, 2005, by Jensen, sent from the USPTO on Jun. 12, 2009.
Final Office Action in U.S. Appl. No. 11/229,427, filed Sep. 15, 2005, by Jensen, sent from the USPTO on Jan. 27, 2009.
Notice of Allowance mailed Apr. 14, 2010 in U.S. Appl. No. 12/154,088 filed May 20, 2008 by Hansen et al.
Notice of Allowance mailed Apr. 8, 2010 in U.S. Appl. No. 11/304,427 filed Dec. 15, 2005 by Jensen et al.
Abandonment mailed on Jun. 10, 2008 in U.S. Appl. No. 11/304,429 filed Dec. 15, 2005 by Hansen et al.
Non-Final Office Action mailed Nov. 20, 2007 in U.S. Appl. No. 11/304,429 filed Dec. 15, 2005 by Hansen et al.
Non-Final Office Action mailed Apr. 18, 2007 in U.S. Appl. No. 11/304,429 filed Dec. 15, 2005 by Hansen et al.
Abandonment mailed Apr. 7, 2009 in U.S. Appl. No. 11/450,783 filed Jun. 9, 2006 by Hansen et al.

Non-Final Office Action mailed Sep. 19, 2008 in U.S. Appl. No. 11/450,783 filed Jun. 9, 2006 by Hansen et al.
Bach, Ronald et al., Blood, vol. 63, Part 2, pp. 393-398 (1984).
Bajaj, S. Paul et al, Journal of Biological Chemistry, vol. 256, Part 1, pp. 253-259 (1981).
Broze, Jr., George J. et al., Journal of Biological Chemistry, vol. 255, Part 4, pp. 1242-1247 (1980).
Brozovic et al., J. Clin. Path., 1971, vol. 24, pp. 690-693.
Dike et al., British Journal of Haematology, vol. 45 pp. 107-118 (1980).
Dombrose et al., Thrombosis Research, vol. 3, pp. 737-743 (1973).
International Search Report Mailed Feb. 9, 2005 for PCT/DK2004/000181.
International Search Report Mailed July 22, 2004 for PCT/DK2004/000183.
Jesty, Jolyon et al, Journal of Biological Checmistry, vol. 249, Part 2, pp. 509-515 (1974).
Klausen, N. K. et al., Analysis of the Glycoforms of human recombinant factor VIIa by capillary electrophoresis and high-performance liquid chromatography, Journal of Chromatography, vol. 718, pp. 195-202 (1995).
Liebman, Howard A. et al., Proceedings of the National Academy of Sciences of the USA, vol. 82, pp. 3879-3883 (1985).
Nemerson, Yale et al, Proceedings of the National Academy of Sciences of the USA, vol. 70, Part 2, pp. 310-314 (1973).
Non-final Office Action mailed Oct. 1, 2008 in U.S. Appl. No. 11/229,428 filed on Sep. 15, 2005 by Krarup et al.
Notice of Allowance mailed Jan. 12, 2010 in U.S. Appl. No. 11/229,428 filed on Sep. 15, 2005 by Krarup et al.
Notice of Allowance mailed Aug. 28, 2009 in U.S. Appl. No. 11/229,428 filed on Sep. 15, 2005 by Krarup et al.
Notice of Allowance mailed May 28, 2009 in U.S. Appl. No. 11/229,428 filed on Sep. 15, 2005 by Krarup et al.
O'Brien, Donogh P. et al, Blood, vol. 78, Part 1, pp. 132-140 (1991).
Rao, L.V.M. et al, Analytical Biochemistry, vol. 136, Part 2, pp. 357-361 (1984).
Ruiz, Sonia M., et al, Thrombosis Research, vol. 98, pp. 203-211 (2000).
Tomokiyo, K. et al., Large-scale production and properties of human plasma-derived activated Factor VII concentrate, Vox Sanguinis, vol. 84, pp. 54-64 (2003).
Yan, S. Betty, Journal of Molecular Recognition, vol. 9 pp. 211-218 (1996).
Final Office Action mailed on May 2, 2008 in U.S. Appl. No. 11/304,427 filed Dec. 15, 2005 by Jensen et al.
Husi et al., 1999, "Separation of Human Vitamin K-Dependent Coagulation Proteins Using Hydrophobic Interaction Chromatography," Journal of Chromatography B 736:77-88.
Krarup et al., 2003, "Studies on Coagulation Factor VIIA . . ." Abstracts of Papers-American Chemical Society 225(1-2):201-202 Abstract #BIOT333.
English Translation of Krylov, Chief Editor, 2001, Enziklopedia Lekarstv. M., (Encyclopaedia of Medicines/Drugs) RLS-2001, 468; Encyclopedia of Drugs, pp. 468.
Novo Nordisk, 1999, "Novoseven Coagulation Factor VIIA (Recombinant)," FDA Article Online pp. 1-24.
PCT/DK2004/000181 International Search Report, dated Feb. 9, 2005.
PCT/DK2004/000359 International Search Report dated Oct. 1, 2004.
PCT/DK03/00419 International Search Report, dated Oct. 20, 2003.
Sichler et al., 2002, "Crystal Structures of Uninhibited Factor VIIa Link its Cofactor and Substrate-Assisted Activation to Specific Interactions," J. Molecular Biology 322(3):591-603.
Wang et al., 1988, "Parenteral Drug Association Objectives," Journal of Parenteral Science & Technology 42:2S.
DE 19853033 English Abstract May 25, 2000.
EP 765669 English Abstract Apr. 2, 1997.
JP 11-500408 English Language Machine Translation, published Jan. 12, 1999 (ZymoGenetics and Novo Nordisk A/S).
JP 6-504678 English Abstract, Mar. 9, 2010.
JP 62-195335 English Abstract, Mar. 9, 2010.
Non-Final Office Action mailed Jun. 8, 2010 in U.S. Appl. No. 12/617,471 filed Nov. 12, 2009 by Jensen et al.
Non-Final Office Action mailed Jul. 2, 2010 in U.S. Appl. No. 12/536,872 filed Aug. 6, 2009 by Jensen et al.
Non-Final Office Action mailed Jul. 7, 2010 in U.S. Appl. No. 12/407,266 filed Mar. 19, 2009 by Hansen et al.
Notice of Allowance mailed Jul. 30, 2010 in U.S. Appl. No. 12/154,088 filed May 20, 2008 by Hansen et al.
Notice of Abandonment mailed Jul. 14, 2010 in U.S. Appl. No. 11/473,387 filed Jun. 21, 2006 by Hansen et al.
Notice of Allowance mailed Aug. 11, 2009 in U.S. Appl. No. 11/353,335 filed Feb. 14, 2006 by Jensen et al.
Non-Final Office Action mailed Jan. 13, 2009 in U.S. Appl. No. 11/353,335 filed Feb. 14, 2006 by Jensen et al.
Non-Final Office Action mailed Jul. 11, 2008 in U.S. Appl. No. 11/353,335 filed Feb. 14, 2006 by Jensen et al.
Advisory Action mailed Oct. 23, 2008 in U.S. Appl. No. 11/304,427 filed Dec. 15, 2005 by Jensen et al.
Notice of Abandonment mailed Apr. 17, 2007 in U.S. Appl. No. 11/304,427 filed Dec. 15, 2005 by Jensen et al. and Decision of Petition to Reinstate Granted.
Non-Final Office Action mailed Aug. 27, 2010 in U.S. Appl. No. 11/284,709 filed Nov. 22, 2005 by Jensen et al.
Final Office Action mailed Feb. 19, 2010 in U.S. Appl. No. 11/284,709 filed Nov. 22, 2005 by Jensen et al.
Non-Final Office Action mailed Jun. 4, 2009 in U.S. Appl. No. 11/284,709 filed Nov. 22, 2005 by Jensen et al.
Non-Final Office Action mailed Sep. 25, 2008 in U.S. Appl. No. 11/284,709 filed Nov. 22, 2005 by Jensen et al.
Non-Final Office Action mailed Aug. 6, 2007 in U.S. Appl. No. 11/284,709 filed Nov. 22, 2005 by Jensen et al.
Notice of Allowance mailed May 6, 2010 in U.S. Appl. No. 11/229,428 filed Sep. 15, 2005 by Krarup et al.
Advisory Action mailed Apr. 8, 2009 in U.S. Appl. No. 11/229,427 filed Sep. 15, 2005 by Jensen et al.
Advisory Action mailed Aug. 3, 2007 in U.S. Appl. No. 10/427,395 filed May 1, 2003 by Nedergaard et al.
Blajchman, 2001, "Novel platelet products, substitutes and alternatives," Transfusion Clinique et Biologique 8(3):267-271.
JP 2000-302689 Machine Translation published Oct. 31, 2000.
Final Office Action mailed Aug. 26, 2010 in U.S. Appl. No. 11/526,503 filed Sep. 25, 2006 by Jensen et al.
Non-Final Office Action mailed Nov. 12, 2010 in U.S. Appl. No. 11/526,503 filed Sep. 25, 2006 by Jensen et al.
Moscardo et al., British Journal of Haematology, 2001, vol. 113, pp. 174-176.
Shapiro et al., Thrombosis and Haemostasis, 1998, vol. 80, pp. 773-778.
Jonathan Marmur, Thrombosis, Hemostasis, and Blood Clotting, http://www.marmur.com/thrombosis-hemostasis-and-blood-clotting.pp. 1-11, Dec. 13, 2010.
Non-Final Office Action issued Dec. 17, 2010 in U.S. Appl. No. 12/325,348 by Nedergaard.
Non-Final Office Action issued Dec. 20, 2010 in U.S. Appl. No. 12/407,266 by Hansen.

* cited by examiner

Figure 1

LIQUID COMPOSITION OF FACTOR VII POLYPEPTIDES

CROSS-REFERENCE TO RELATED APPLICATIONS

This application is a Continuation-in-Part of International Application No. PCT/DK02/00895 filed Dec. 20, 2002 and claims priority under 35 U.S.C. 119 of Danish application no. PA 2001 01948 filed Dec. 21, 2001 and U.S. application No. 60/346,888 filed Jan. 7, 2002, and claims priority under 35 U.S.C. 120 of international application no. PCT/DK02/00895 filed Dec. 20, 2002, the contents of which are fully incorporated herein by reference.

FIELD OF THE INVENTION

The present invention is directed to liquid aqueous compositions containing factor VII polypeptides, and to methods for making and using such compositions. More particularly, this invention relates to liquid compositions stabilized against chemical and/or physical degradation.

BACKGROUND OF THE INVENTION

A variety of factors involved in the blood clotting process have been identified, including factor VII (FVII), a plasma glycoprotein. Haemostasis is initiated by the formation of a complex between tissue factor (TF) being exposed to the circulating blood following an injury to the vessel wall, and FVIIa which is present in the circulation in an amount corresponding to about 1% of the total FVII protein mass. FVII exists in plasma mainly as a single-chain zymogen, which is cleaved by FXa into its two-chain, activated form, FVIIa. Recombinant activated factor VIIa (rFVIIa) has been developed as a pro-haemostatic agent. The administration of rFVIIa offers a rapid and highly effective pro-haemostatic response in haemophilic subjects with bleedings who cannot be treated with other coagulation factor products due to antibody formation. Also bleeding in subjects with factor VII deficiency or subjects having a normal coagulation system but experiencing excessive bleeding can be treated successfully with FVIIa.

It is desirable to have administration forms of factor VIIa suitable for both storage and for delivery. Ideally, the drug product is stored and administered as a liquid. Alternatively, the drug product is lyophilized, i.e., freeze-dried, and then reconstituted by adding a suitable diluent just prior to patient use. Ideally, the drug product has sufficient stability to be kept in long-term storage, i.e., more than six months.

The decision to either maintain the finished drug product as a liquid or to freeze-dry it is usually based on the stability of the protein drug in those forms. Protein stability can be affected inter alia by such factors as ionic strength, pH, temperature, repeated cycles of freeze/thaw, and exposures to shear forces. Active protein may be lost as a result of physical instabilities, including denaturation and aggregation (both soluble and insoluble aggregate formation), as well as chemical instabilities, including, for example, hydrolysis, deamidation, and oxidation, to name just a few. For a general review of stability of protein pharmaceuticals, see, for example, Manning, et al., Pharmaceutical Research 6:903-918 (1989).

While the possible occurrence of protein instabilities is widely appreciated, it is impossible to predict particular instability problems of a particular protein. Any of these instabilities can result in the formation of a protein by-product, or derivative, having lowered activity, increased toxicity, and/or increased immunogenicity. Indeed, protein precipitation may lead to thrombosis, non-homogeneity of dosage form and amount, as well as clogged syringes. Furthermore, post-translational modifications such as, for example, gamma carboxylation of certain glutamic acid residues in the N-terminus and addition of carbohydrate side chains provide potential sites that may be susceptible to modification upon storage. Also, specific to factor VIIa, being a serine protease, fragmentation due to autocatalysis may occur (enzymatic degradation). Thus, the safety and efficacy of any composition of a protein is directly related to its stability. Maintaining stability in a liquid form is generally different from a lyophilized form because of greatly increased potential for molecular motion and therefore increased probability of molecular interactions. Maintaining stability in a concentrated form is also different because of the propensity for aggregate formation at increased protein concentrations.

When developing a liquid composition, many factors are taken into consideration. Short-term, i.e., less than six months, liquid stability generally depends on avoiding gross structural changes, such as denaturation and aggregation. These processes are described in the literature for a number of proteins, and many examples of stabilizing agents exist. It is well known that an agent effective at stabilizing one protein actually acts to destabilize another. Once the protein has been stabilized against gross structural changes, developing a liquid composition for long-term stability (e.g., greater than six months) depends on further stabilizing the protein from types of degradation specific to that protein. More specific types of degradation may include, for example, disulfide bond scrambling, oxidation of certain residues, deamidation, cyclization. Although it is not always possible to pinpoint the individual degradation species, assays are developed to monitor subtle changes so as to monitor the ability of specific excipients to uniquely stabilize the protein of interest.

In addition to stability considerations, one generally selects excipients, which are approved by various worldwide medical regulatory agencies. It is desirable that the pH of the composition is in a physiologically suitable range upon injection/infusion, otherwise pain and discomfort for the patient may result.

For a general review of protein compositions, see, for example, Cleland et al.: The development of stable protein compositions: A closer look at protein aggregation, deamidation and oxidation, Critical Reviews in Therapeutic Drug Carrier Systems 1993, 10(4): 307-377; and Wang et al., Parenteral compositions of proteins and peptides: Stability and stabilizers, Journal of Parenteral Science and Technology 1988 (Supplement), 42 (2S).

Other publications of interest regarding stabilization of proteins are as follows.

U.S. 20010031721 A1 (American Home Products) concerns highly concentrated, lyophilized, and liquid factor IX compositions.

U.S. Pat. No. 5,770,700 (Genetics Institute) concerns liquid factor IX compositions.

WO 97/19687 (American Red Cross) concerns liquid compositions of plasma proteins, in particular factor VIII and factor IX.

U.S. Pat. No. 4,297,344 discloses stabilization of coagulation factors II and VIII, antithrombin III, and plasminogen against heat by adding selected amino acids such as glycine, alanine, hydroxyproline, glutamine, and aminobutyric acid, and a carbohydrate such as a monosaccharide, an oligosaccharide, or a sugar alcohol.

Factor VIIa undergoes several degradative pathways, especially aggregation (dimerisation), oxidation, and autolytic cleavage (clipping of the peptide backbone). Furthermore, precipitation may occur. Many of these reactions can be slowed significantly by removal of water from the protein. However, the development of an aqueous composition for factor VIIa has the advantages of eliminating reconstitution errors, thereby increasing dosing accuracy, as well as simplifying the use of the product clinically, thereby increasing patient compliance. Ideally, compositions of factor VIIa should be stable for more than 6 months over a wide range of protein concentrations. This allows for flexibility in methods of administration. Generally, more highly concentrated forms allow for the administration of lower volumes, which is highly desirable from the patients' point of view. Liquid compositions can have many advantages over freeze-dried products with regard to ease of administration and use.

Today, the only commercially available, recombinantly-made FVII polypeptide composition is a freeze-dried factor FVIIa product which is reconstituted before use; it contains a relatively low factor VIIa concentration, e.g., about 0.6 mg/ml. A vial (1.2 mg) of NovoSeven® (Novo Nordisk A/S, Denmark) contains 1.2 mg recombinant human factor VIIa, 5.84 mg NaCl, 2.94 mg CaCl2, 2H2O, 2.64 mg GlyGly, 0.14 mg polysorbate 80, and 60.0 mg mannitol; it is reconstituted to pH 5.5 by 2.0 ml water for injection (WFI). When reconstituted, the protein solution is stable for use for 24 hours. Thus, no liquid ready-for use- or concentrated factor VII products are currently commercially available.

Accordingly, there is a need in the art for methods for improving stability of factor VII polypeptides, including human factor VIIa (chemical and/or physical stability), increasing the concentration, maintaining activity levels, and providing liquid compositions suitable for storage. Thus, it is an objective of this invention to provide an aqueous factor VII polypeptide composition which provides acceptable control of chemical and/or physical degradation products such as enzymatic degradation or autocatalysis products.

SUMMARY OF THE INVENTION

The present inventors have discovered that factor VII or analogues thereof ("factor VII polypeptides"), when formulated in aqueous solution together with a buffering agent, and a calcium or magnesium salt or mixture thereof at a concentration of at least 15 mM, are stable in the pH range from about 4 to about 8.

In one aspect, the present invention provides a liquid aqueous composition comprising (i) a factor VII polypeptide, (ii) an agent suitable for keeping pH in the range of from about 4.0 to about 8.0; and (iii) an agent selected from the list of: a calcium salt, a magnesium salt, or a mixture thereof; wherein the concentration of (iii) is at least 15 mM.

In different embodiments, the agent (iii) is present in a concentration of at least about 25 mM, 50 mM, 100 mM, 200 mM, 400 mM, 800 mM, 900 mM, or at least 1000 mM.

In another embodiment, the composition further comprises (iv) a ionic strength modifying agent.

In different embodiments, the ionic strength modifying agent is selected from the list of: a neutral salt, e.g., sodium chloride; an amino acid; or a small peptide, or a mixture of at least two of said modifying agents. In a preferred embodiment, the ionic strength modifying agent is sodium chloride.

In different embodiments, the agent (iv) is present in a concentration of at least about 5 mM, 10 mM, 20 mM, 50 mM, 100 mM, 200 mM, 400 mM, 800 mM, 1000 mM, 1200 mM, 1500 mM, 1800 mM, 2000 mM, or at least 2200 mM.

In one series of embodiments, the agent (iii) (calcium and/or magnesium salt) is present in a concentration of from about 15 mM to about 1000 mM, such as from about 25 mM to about 1000 mM, from about 50 mM to about 1000 mM, from about 100 mM to about 1000 mM, from about 200 mM to about 1000 mM, from about 300 mM to about 1000 mM, from about 400 mM to about 1000 mM, from about 500 mM to about 1000 mM, from about 600 mM to about 1000 mM, from about 700 mM to about 1000 mM; from about 15 mM to about 800 mM, from about 25 mM to about 800 mM, from about 50 mM to about 800 mM, from about 100 mM to about 800 mM, from about 200 mM to about 800 mM, from about 300 mM to about 800 mM, from about 400 mM to about 800 mM, from about 500 mM to about 800 mM; from about 15 mM to about 600 mM, from about 25 mM to about 600 mM, from about 50 mM to about 600 mM, from about 100 mM to about 600 mM, from about 200 mM to about 600 mM, from about 300 mM to about 600 mM; from about 15 mM to about 400 mM, from about 25 mM to about 400 mM, from about 50 mM to about 400 mM, or from about 100 mM to about 400 mM.

In one series of embodiments, the agent (iv) (ionic strength modifying agent) is present in a concentration of from about 5 mM to about 2200 mM, such as from about 25 mM to about 2200 mM, from about 50 mM to about 2200 mM, from about 100 mM to about 2200 mM, from about 200 mM to about 2200 mM, from about 400 mM to about 2200 mM, from about 600 mM to about 2200 mM, from about 800 mM to about 2200 mM, from about 1000 mM to about 2200 mM, from about 1200 mM to about 2200 mM, from about 1400 mM to about 2200 mM, from about 1600 mM to about 2200 mM, from about 1800 mM to about 2200 mM, or from about 2000 mM to about 2200 mM; from about 5 mM to about 1800 mM, from about 25 mM to about 1800 mM, from about 50 mM to about 1800 mM, from about 100 mM to about 1800 mM, from about 200 mM to about 1800 mM, from about 400 mM to about 1800 mM, from about 600 mM to about 1800 mM, from about 800 mM to about 1800 mM, from about 1000 mM to about 1800 mM, from about 1200 mM to about 1800 mM, from about 1400 mM to about 1800 mM, from about 1600 mM to about 1800 mM; from about 5 mM to about 1500 mM, from about 25 mM to about 1400 mM, from about 50 mM to about 1500 mM, from about 100 mM to about 1500 mM, from about 200 mM to about 1500 mM, from about 400 mM to about 1500 mM, from about 600 mM to about 1500 mM, from about 800 mM to about 1500 mM, from about 1000 mM to about 1500 mM, from about 1200 mM to about 1500 mM; from about 5 mM to about 1200 mM, from about 25 mM to about 1200 mM, from about 50 mM to about 1200 mM, from about 100 mM to about 1200 mM, from about 200 mM to about 1200 mM, from about 400 mM to about 1200 mM, from about 600 mM to about 1200 mM, or from about 800 mM to about 1200 mM.

In one preferred embodiment, the total concentration of agents (iii) and (iv) is from about 50 mM to about 2500 mM, such as from about 100 mM to about 2500 mM, from about 200 mM to about 2500 mM, from about 400 mM to about 2500 mM, from about 600 mM to about 2500 mM, from about 800 mM to about 2500 mM, from about 1000 mM to about 2500 mM, from about 1200 mM to about 2500 mM, from about 1400 mM to about 2500 mM, from about 1600 mM to about 2500 mM, from about 1800 mM to about 2500 mM, or from about 2000 mM to about 2500 mM; from about 50 mM to about 2000 mM, from about 100 mM to about 2000 mM, from about 200 mM to about 2000 mM, from about 400 mM to about 2000 mM, from about 600 mM to about 2000 mM, from about 800 mM to about 2000 mM, from about 1000 mM to about 2000 mM, from about 1200 mM to about 2000 mM, from about 1400 mM to about 2000 mM, or from about 1600 mM to about 2000 mM; from about 50 mM to about 1600 mM, from about 100 mM to about 1600 mM, from about 200 mM to about 1600 mM, from about 400 mM to about 1600 mM, from about 600 mM to about 1600 mM, from about 800 mM to about 1600 mM, from about 1000 mM to about 1600 mM, or from about 1200 mM to about 1600 mM.

In one embodiment, the agents (iii) and (iv) are present in concentrations of from about 600 to about 800 mM of (iii) and from 0 to about 5 mM of (iv); in another embodiment, the agents (iii) and (iv) are present in concentrations of from about 300 to about 500 mM of (iii) and from about 1100 to about 1300 mM of (iv); in another embodiment, the agents (iii) and (iv) are present in concentrations of from about 100 to about 300 mM of (iii) and from about 1500 to about 1900 mM of (iv); in yet another embodiment, the agents (iii) and (iv) are present in concentrations of from about 50 to about 150 mM of (iii) and from about 1800 about 2300 mM of (iv).

In different embodiments, the ionic strength of the composition is at least 50, such as at least 75,100 150, 200, 250, 400, 500, 650, 800, 1000, 1200, 1600, 2000, 2400, 2800, or at least 3200.

In different embodiments, the calcium salt is selected from the list of: calcium chloride, calcium acetate, calcium gluconate, and calcium laevulate. In different embodiments, the magnesium salt is selected from the list of: magnesium chloride, magnesium acetate, magnesium sulphate, magnesium gluconate, magnesium laevulate, and salts of strong acids.

In preferred embodiments, the agent (iii) is selected from the list of: calcium chloride, calcium acetate, magnesium chloride, magnesium acetate, magnesium sulphate, or a mixture thereof; and the ionic strength modifying agent (iv) is sodium chloride.

In a further embodiment, the composition further comprises (v) a tonicity modifying agent.

In different embodiments, the tonicity modifying agent (v) is selected from the list of: a neutral salt; a mono-, di- or polysaccharide; a sugar alcohol; an amino acid; or a small peptide, or a mixture of at least two of said modifying agents.

In one embodiment, the tonicity modifying agent (v) is present in a concentration of from about 1 to about 500 mM; from about 1 to about 300 mM; from about 10 to about 200 mM; or from about 20 to about 150 mM.

In a further embodiment, the composition further comprises (vi) a non-ionic surfactant.

In one embodiment, the non-ionic surfactant is present in an amount of from about 0.005 to about 2.0% by weight.

In different embodiments, the non-ionic surfactant is a polysorbate or a poloxamer or a polyoxyethylene alkyl ether; preferably poloxamer 188 or poloxamer 407, or polysorbate 20 or polysorbate 80, or polyoxy 23 lauryl ether.

In a further embodiment, the composition further comprises (vii) an antioxidant. In different embodiments, the antioxidant is D- or L-methionine; a methionine analogue; a methion-ine-containing peptide; ascorbic acid; cysteine; a methionine- homologue, e.g., homocysteine; gluthatione,. In a preferred embodiment, the antioxidant is L-methionine. In one embodiment, the antioxidant is present in a concentration of from about 0.1 to about 5.0 mg/ml.

In one embodiment, the pH of the composition is kept from about 4.0 to about 7.0; such as from about 4.5 to about 7.0; from about 5.0 and about 7.0; from about 5.5 to about 7.0; or from about 6.0 to about 7.0.

In one embodiment, the agent suitable for keeping pH in the range of from about 4.0 to about 8.0 is a buffering agent selected from the list of acids and salts of: citrate, acetate, histidine, malate, phosphate, tartaric acid, succinic acid, MES, HEPES, Imidazol, TRIS, lactate, glycylglycin, PIPES, glycin, or a mixture of at least two of said buffering agents.

In one embodiment, the concentration of the buffering agent is from about 1 mM to 100 mM; from 1 mM to about 50 mM; from about 1 mM to about 25 mM; from about 2 mM to about 20 mM; or about 10 mM.

In a further embodiment, the composition further comprises (viii) a preservative. In one embodiment, the preservative is selected from the list of phenol, benzyl alcohol, orto-cresol, meta-cresol, para-cresol, methyl paraben, propyl paraben, benzalconium chloride and benzaethonium chloride.

In one embodiment, the composition is isotonic; in another, it is hypertonic. In one embodiment, the composition is formulated for pharmaceutical administration. In one embodiment, the composition is stable and/or stabilized for at least 6 months at 2-8° C.

In different embodiments, the factor VII polypeptide is human factor VIIa; recombinant human factor VIIa; a factor VII-related polypeptide; a factor VII sequence variant; or a factor VII polypeptide wherein the activity of the factor VII polypeptide and the activity of native human Factor VIIa (wild-type FVIIa) is at least about 1.25, preferably at least about 2.0, or 4.0, most preferred at least about 8.0, when tested in the "In Vitro Proteolysis Assay" as described in the present specification. In one embodiment, the factor VII polypeptide has a glycosylation different from wild-type human factor VII.

In different embodiments, the factor VII polypeptide is present in a concentration of from about 0.1 mg/ml to about 10 mg/ml; from about 0.5 mg/ml to about 5.0 mg/ml; from about 0.6 mg/ml to about 4.0 mg/ml; from about 1.0 mg/ml to about 4.0 mg/ml; from about 0.1 mg/ml to about 5 mg/ml; from about 0.1 mg/ml to about 4.0 mg/ml; from about 0.1 mg/ml to about 2 mg/ml; or from about 0.1 mg/ml to about 1.5 mg/ml.

In a further aspect, the invention also provides a method for preparing a liquid, aqueous composition of a factor VII polypeptide, comprising the step of providing the factor VII polypeptide in a solution comprising (i) A factor VII polypeptide; (ii) An agent suitable for keeping pH in the range of from about 4.0 to about 8.0; (iii) An agent selected from the list of: a calcium salt, a magnesium salt, or a mixture thereof; wherein the concentration of (iii) is at least 15 mM.

In a yet further aspect, the invention also concerns the use of the composition for the preparation of a medicament for treating a factor VII-responsive syndrome.

In a further aspect, the present invention relates to a method for treating a factor VII responsive syndrome, the method comprising administering to a subject in need thereof, under conditions that result in a decrease in bleeding and/or an increase in blood clotting, an effective amount of an aqueous liquid composition comprising (i) a factor VII polypeptide, (ii) an agent suitable for keeping pH in the range of from about 4.0 to about 8.0; (iii) an agent selected from the list of: a calcium salt, a magnesium salt, or a mixture thereof; wherein the concentration of (iii) is at least 15 mM.

In different embodiments, the syndrome is selected from the group consisting of haemophilia A, haemophilia B, Factor XI deficiency, Factor VII deficiency, thrombocytopenia, von Willebrand's disease, presence of a clotting factor inhibitor, surgery, intra cerebral haemorrhage, trauma, and anticoagulant therapy.

DETAILED DESCRIPTION OF THE INVENTION

The compositions according to the present invention are useful as stable and preferably ready-to-use compositions of factor VII polypeptides. The compositions are stable for at least six months, and preferably up to 36 months; when stored at temperatures ranging from 2° to 8° C. The compositions are chemically and/or physically stable, in particular chemically stable, when stored for at least 6 months at from 2° to 8° C.

"Stable" is intended to mean that the composition, after storage for 6 months at 2 to 8° C. retains at least 50% of its initial biological activity as measured by a one-stage clot assay essentially as described in WO 92/15686 (Example II). In short, the sample to be tested is diluted in 50 mM Tris (pH 7.5), 0.1% BSA and 100 µl is incubated with 100 µl of Factor VII deficient plasma and 200 µl of thromboplastin C containing 10 mM $Ca^{2+}$. Clotting times are measured and compared to a standard curve using a reference standard or a pool of citrated normal human plasma in serial dilution.

Preferably, the stable composition retains at least 80% of its initial activity after storage for 6 months at 2 to 8° C.

The term "stabilized", which may be used interchangeably with "relatively stable", is intended to mean that the composition, after storage for at least 6 months at 2 to 8° C., contains a lesser amount of at least one of the following degradation products: (i) enzymatic degradation products, (ii) aggregates (dimers, oligomers, polymers), (iii) oxidized forms, (iv) deamidated forms, relative to the amount of corresponding degradation product(s) contained in a solution of reconstituted NovoSeven® product which has been stored under similar conditions for a similar period of time.

The term "physically stable" is intended to designate a composition which remains visually clear. Physical stability of the compositions is evaluated by means of visual inspection and turbidity after storage of the composition at different temperatures for various time periods. Visual inspection of the compositions is performed in a sharp focused light with a dark background. A composition is classified physical unstable, when it shows visual turbidity.

The term "physical stability" of Factor VII polypeptides relates to the formation of insoluble and/or soluble aggregates in the form of dimeric, oligomeric and polymeric forms of Factor VII polypeptides as well as any structural deformation and denaturation of the molecule.

The term "chemically stable" is intended to designate a composition which retains at least 50% of its initial biological activity after storage for 6 months at 2 to 8° C., as measured by a one-stage clot assay essentially as described in WO 92/15686.

The term "chemical stability" is intended to relate to the formation of any chemical change in the Factor VII polypeptides upon storage in solution at accelerated conditions. By example are hydrolysis, deamidation and oxidation as well as enzymatic degradation resulting in formation of fragments of factor VII polypeptides, In particular, the sulphur-containing amino acids are prone to oxidation with the formation of the corresponding sulphoxides.

The compositions comprise factor VII polypeptides, calcium and/or magnesium ions, buffering agents, and, optionally, other excipients, which further stabilize the factor VII polypeptides, including ionic strength modifying agents and tonicity modifiers. The factor VII polypeptides concentration ranges from about 0.1 to about 10 mg/mL.

As used herein, the term "ionic strength modifying agent" includes agents, which contribute to the ionic strength of the solution. The agents include, but are not limited to, neutral salts, e.g., sodium chloride or potassium chloride; amino acids; small peptides (e.g., having from 2 to 5 amino acid residues such as, e.g., glycylglycine), or a mixture of at least two of said modifying agents. A preferred agent is sodium chloride. The ionic strength modifying agents are present in a concentration of at least about 5 mM, 10 mM, 20 mM, 50 mM, 100 mM, 200 mM, 400 mM, 800 mM, 1000 mM, 1200 mM, 1500 mM, 1800 mM, 2000 mM, or at least 2200 mM.

As used herein, the term "tonicity modifier" includes agents, which contribute to the osmolality of the solution. Tonicity modifiers include, but are not limited to, amino acids; small peptides (e.g., having from 2 to 5 amino acid residues); neutral salts; mono- or disaccharides; polysaccharides; sugar alcohols, or a mixture of at least two of said modifiers. Examples of tonicity modifiers include, but are not limited to, sodium chloride, potassium chloride, sodium citrate, sucrose, glucose, glycylglycine, and mannitol. Normally, the modifiers are present at a concentration of from about 1 to about 500 mM; from about 1 to about 300 mM; from about 10 to about 200 mM; or from about 20 to about 150 mM, depending on the other ingredients present. Neutral salts such as, e.g., sodium chloride or potassium chloride may be used.

By "neutral salt" is meant a salt that is neither an acid nor a base when dissolved in aqueous solution.

The term "agent suitable for keeping the pH in the range of about 4.0 to about 8.0" encompasses those agents, which maintain the solution pH in an acceptable range from about 4.0 to about 8.0, such as from about 4.0 to about 7.0, from about 4.5 to about 7.0, from about 5.0 to about 7.0, from about 5.0 to about 6.5, from about 5.5 to about 7.0, from about 5.5 to about 6.5, from about 6.0 to about 7.0, from about 5.0 to about 6.0, from about 6.4 to about 6.6, or about 6.5, from about 5.2 to about 5.7, or about 5.5. The term may be used interchangeably with "buffering agent" These may include, but are not limited to, acids and salt of: citrate (sodium or potassium), acetate (ammonium, sodium or calcium), histidine (L-histidine), malate, phosphate (sodium or potassium), tartaric acid, succinic acid, MES, HEPES, imidazol, TRIS, lactate, glutamate, glycylglycin, PIPES, glycin, or a mixture of at least two of said buffering agents. The buffer concentration range is chosen to maintain the preferred pH of the solution. The buffering agent may also be a mixture of at least two buffering agents, wherein the mixture is able to provide a pH value in the specified range. In alternative embodiments, the buffer concentration is in the range of from about 1 mM to 100 mM; from 1 mM to about 50 mM; from about 1 mM to about 25 mM; from about 2 mM to about 20 mM; or about 10 mM.

Optionally, the compositions may also contain a surfactant or detergent. "Surfactants" or "detergents" generally include those agents which protect the protein from air/solution interface induced stresses and solution/surface induced stresses (e.g., resulting in protein aggregation). The detergent is preferably a non-ionic detergent including, but not limited to polysorbates (e.g. Tween®), such as polysorbate 20 or 80; polyoxyethylene alkyl ethers or poloxamers, such as poloxamer 188 or 407, (e.g., Pluronic® polyols) and other ethylene/polypropylene block polymers, or polyethyleneglycol (PEG) such as PEG8000. The amount of surfactant present ranges from about 0.005 to about 2.0%.

Optionally, the composition may include an antioxidant. Antioxidants include, but are not limited to, ascorbic acid, cysteine, homocysteine, cystine, cysstathionine, methionine, gluthatione, and other peptides containing cysteine or methionine, in particular peptides with 2 to 5 amino acid residues wherein at least one of the residues is a methionine or cysteine residue; methionine, in particular L-methionine, is preferred. The antioxidant is included at a concentration of 0.1 to 5 mg/ml, such as 0.1 to 4, 0.1 to 3, 0.1 to 2, or 0.5 to 2 mg/ml.

A preservative may also be included in the composition to retard microbial growth and thereby allow "multiple use" packaging of the FVII polypeptides. Preservatives include phenol, benzyl alcohol, orto-cresol, meta-cresol, para-cresol, methyl paraben, propyl paraben, benzalconium chloride, and benzethonium chloride. The preservative is normally included at a concentration of 0.1 to 20 mg/ml depending on pH range and type of preservative. Optionally, the composition may also include an agent capable of inhibiting deamidation.

As used herein, amounts specified are understood to be ± about 10%, e.g., about 50 mM includes 50 mM±5 mM; e.g., 4% includes 4% ±0.4%, etc.

Percentages are (weight/weight) both when referring to solids dissolved in solution and liquids mixed into solutions. For example, for Tween, it is the weight of 100% stock/weight of solution.

The term "ionic strength" is the ionic strength of the solution ($\mu$) which is defined by the equation:

$$\mu = \tfrac{1}{2}\Sigma([i](Z_i^2)),$$

where $\mu$ is the ionic strength, [i] is the molar concentration of an ion, and $Z_i$ is the charge (+ or −) of that ion (James Fritz and George Schenk: Quantitative Analytical Chemistry, 1979). In different embodiments of the invention, the ionic strength of the composition is at least 50, such as at least 75, 100 150, 200, 250, 400, 500, 650, 800, 1000, 1200, 1600, 2000, 2400, 2800, or at least 3200.

The term "isotonic" means "isotonic with serum", i.e., at about 300±50 milliosmol/kg. The tonicity is meant to be a measure of osmolality of the solution prior to administration. The term "hypertonic" is meant to designate levels of osmolality above the physiological level of serum, such as levels above 300±50 milliosmol/kg.

The term "pharmaceutically effective amount" or "effective amount" is the effective dose to be determined by a qualified practitioner, who may titrate dosages to achieve the desired response. Factors for consideration of dose will include potency, bioavailability, desired pharmacokinetic/pharmacodynamic profiles, condition of treatment, patient-related factors (e.g. weight, health, age, etc.), presence of co-administered medications (e.g., anticoagulants), time of administration, or other factors known to a medical practitioner.

The term "treatment" is defined as the management and care of a subject, e.g. a mammal, in particular a human, for the purpose of combating the disease, condition, or disorder and includes the administration of a factor VII polypeptide to prevent the onset of the symptoms or complications, or alleviating the symptoms or complications, or eliminating the disease, condition, or disorder. Pharmaceutical compositions according to the present invention containing a factor VII polypeptide may be administered parenterally to subjects in need of such a treatment. Parenteral administration may be performed by subcutaneous, intramuscular or intravenous injection by means of a syringe, optionally a pen-like syringe. Alternatively, parenteral administration can be performed by means of an infusion pump.

Factor VIIa concentration is conveniently expressed as mg/mL or as IU/mL, with 1 mg usually representing 43000-56000 IU or more.

Methods of Use:

The preparations of the present invention may be used to treat any Factor VII-responsive syndrome, such as, e.g., bleeding disorders, including, without limitation, those caused by clotting factor deficiencies (e.g., haemophilia A and B or deficiency of coagulation factors XI or VII); by thrombocytopenia or von Willebrand's disease, or by clotting factor inhibitors, or excessive bleeding from any cause. The preparations may also be administered to patients in association with surgery or other trauma or to patients receiving anticoagulant therapy.

Factor VII Polypeptides to be Formulated According to the Present Invention:

The terms "human factor VII" or "FVII" denote human factor VII produced by methods including natural source extraction and purification, and by recombinant cell culture systems. Its sequence and characteristics are set forth, for example, in U.S. Pat. No. 4,784,950. The terms likewise cover biologically active human factor VII equivalents, e.g., differing in one or more amino acid(s) in the overall sequence. Furthermore, the terms used in this application are intended to cover substitution, deletion and insertion amino acid variants of factor VII or post-translational modifications. As used herein, "Factor VII polypeptide" encompasses, without limitation, Factor VII, as well as Factor VII-related polypeptides. Factor VII-related polypeptides include, without limitation, Factor VII polypeptides that have either been chemically modified relative to human Factor VII and/or contain one or more amino acid sequence alterations relative to human Factor VII (i.e., Factor VII variants), and/or contain truncated amino acid sequences relative to human Factor VII (i.e., Factor VII fragments). Such factor VII-related polypeptide s may exhibit different properties relative to human Factor VII, including stability, phospholipid binding, altered specific activity, and the like.

The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. The term "Factor VII" is also intended to encompass, without limitation, polypeptides having the amino acid sequence 1-406 of wild-type human Factor VII (as disclosed in U.S. Pat. No. 4,784,950), as well as wild-type Factor VII derived from other species, such as, e.g., bovine, porcine, canine, murine, and salmon Factor VII. It further encompasses natural allelic variations of Factor VII that may exist and occur from one individual to another. Also, degree and location of glycosylation or other post-translation modifications may vary depending on the chosen host cells and the nature of the host cellular environment.

As used herein, "Factor VII-related polypeptides" encompasses, without limitation, polypeptides exhibiting substantially the same or improved biological activity relative to wildtype human Factor VII. These polypeptides include, without limitation, Factor VII or Factor VIIa that has been chemically modified and Factor VII variants into which specific amino acid sequence alterations have been introduced that modify or disrupt the bioactivity of the polypeptide.

It further encompasses polypeptides with a slightly modified amino acid sequence, for instance, polypeptides having a modified N-terminal end including N-terminal amino acid deletions or additions, and/or polypeptides that have been chemically modified relative to human Factor VIIa.

Factor VII-related polypeptides, including variants of Factor VII, exhibiting substantially the same or better bioactivity than wild-type Factor VII, include, without limitation, polypeptides having an amino acid sequence that differs from the sequence of wild-type Factor VII by insertion, deletion, or substitution of one or more amino acids.

Factor VII-related polypeptides, including variants, having substantially the same or improved biological activity relative to wild-type Factor VIIa encompass those that exhibit at least about 25%, preferably at least about 50%, more preferably at least about 75%, more preferably at least about 100%, more preferably at least about 110%, more preferably at least about 120%, and most preferably at least about 130% of the specific activity of wild-type Factor VIIa that has been produced in the same cell type, when tested in one or more of a clotting assay, proteolysis assay, or TF binding assay as described in the present specification.

In some embodiments the Factor VII polypeptides are Factor VII-related polypeptides, in particular variants, wherein the ratio between the activity of said Factor VII polypeptide and the activity of native human Factor VIIa (wild-type FVIIa) is at least about 1.25 when tested in the "In Vitro Hydrolysis Assay" (see "Assays", below); in other embodiments, the ratio is at least about 2.0; in further embodiments, the ratio is at least about 4.0. In some embodiments of the invention, the factor VII polypeptides are Factor VII equivalents, in particular variants, wherein the ratio between the activity of said Factor VII polypeptide and the activity of native human Factor VIIa (wild-type FVIIa) is at least about 1.25 when tested in the "In Vitro Proteolysis Assay" (see "Assays", below); in other embodiments, the ratio is at least about 2.0; in further embodiments, the ratio is at least about 4.0; in further embodiments, the ratio is at least about 8.0.

In some embodiments, the Factor VII polypeptide is human Factor VII, as disclosed, e.g., in U.S. Pat. No. 4,784,950 (wild-type Factor VII). In some embodiments, the Factor VI polypeptide is human Factor VIIa. In one series of embodiments, Factor VII polypeptides include polypeptides that exhibit at least about 90%, preferably at least about 100%, preferably at least about 120%, more preferably at least about 140%, and most preferably at least about 160%, of the specific biological activity of human Factor VIIa.

In some embodiments, the Factor VII polypeptides have an amino acid sequence that differs from the sequence of wild-type Factor VII by insertion, deletion, or substitution of one or more amino acids.

In one series of embodiments, Factor VII polypeptides include polypeptides that exhibit at least about 70%, preferably at least about 80%, more preferably at least about 90%, and most preferable at least about 95%, of identity with the sequence of wild-type Factor VII as disclosed in U.S. Pat. No. 4,784,950. Amino acid sequence homology/identity is conveniently determined from aligned sequences, using a suitable computer program for sequence alignment, such as, e.g., the ClustalW program, version 1.8, 1999 (Thompson et al., 1994, Nucleic Acid Research, 22: 4673-4680).

Non-limiting examples of Factor VII variants having substantially the same or improved biological activity as wild-type Factor VII include S52A-FVII, S60A-FVII (Iino et al., Arch. Biochem. Biophys. 352: 182-192, 1998); L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII; FVIIa variants exhibiting increased TF-independent activity as disclosed in WO 01/83725 and WO 02/22776; FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); and oxidized forms of Factor VIIa (Kornfelt et al., Arch. Biochem. Biophys. 363:43-54, 1999).

Biological Activity of Factor VII Polypeptides:

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively).

For purposes of the invention, biological activity of Factor VII polypeptides ("Factor VII biological activity") may be quantified by measuring the ability of a preparation to promote blood clotting using Factor VII-deficient plasma and thromboplastin, as described, e.g., in U.S. Pat. No. 5,997,864 or WO 92/15686. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by

- Measuring the ability of Factor VIIa or a Factor VII-related polypeptide to produce activated Factor X (Factor Xa) in a system comprising TF embedded in a lipid membrane and Factor X. (Persson et al., J. Biol. Chem. 272:19919-19924, 1997);
- Measuring Factor X hydrolysis in an aqueous system ("In Vitro Proteolysis Assay", see below);
- Measuring the physical binding of Factor VIIa or a Factor VII-related polypeptide to TF using an instrument based on surface plasmon resonance (Persson, FEBS Letts. 413:359-363, 1997); and
- Measuring hydrolysis of a synthetic substrate by Factor VIIa and/or a Factor VII-related polypeptide ("In Vitro Hydrolysis Assay", see below); and
- Measuring generation of thrombin in a TF-independent in vitro system.

Assays Suitable for Determining Biological Activity of Factor VII Polypeptides:

Factor VII polypeptides useful in accordance with the present invention may be selected by suitable assays that can be performed as simple preliminary in vitro tests. Thus, the present specification discloses a simple test (entitled "In Vitro Hydrolysis Assay") for the activity of Factor VII polypeptides.

In Vitro Hydrolysis Assay (Assay 1)

Native (wild-type) factor VIIa and Factor VII polypeptide (both hereafter referred to as "factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to factor VIIa (final concentration 100 nM) in 50 mM Hepes, pH 7.4, containing 0.1 M NaCl, 5 mM CaCl2 and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of Factor VII polypeptide and wild-type factor VIIa:

Ratio=(A405 nm Factor VII polypeptide)/(A405 nm factor VIIa wild-type).

Based thereon, Factor VII polypeptides with an activity lower than, comparable to, or higher than native factor VIIa may be identified, such as, for example, Factor VII polypeptides where the ratio between the activity of the Factor VII polypeptide and the activity of native factor VII (wild-type FVII) is about, versus above 1.0.

The activity of the Factor VII polypeptides may also be measured using a physiological substrate such as factor X ("In Vitro Proteolysis Assay"), suitably at a concentration of 100-1000 nM, where the factor Xa generated is measured after the addition of a suitable chromogenic substrate (eg. S-2765). In addition, the activity assay may be run at physiological temperature.

In Vitro Proteolysis Assay (Assay 2)

Native (wild-type) Factor VIIa and Factor VII polypeptide (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM CaCl2 and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of Factor VII polypeptide and wild-type Factor VIIa:

Ratio=(A405 nm Factor VII polypeptide)/(A405 nm Factor VIIa wild-type).

Based thereon, Factor VII polypeptide with an activity lower than, comparable to, or higher than native factor VIIa may be identified, such as, for example, Factor VII polypeptides where the ratio between the activity of the Factor VII polypeptide and the activity of native factor VII (wild-type FVII) is about, versus above 1.0.

The ability of factor VIIa or Factor VII polypeptides to generate thrombin can also be measured in an assay (assay 4) comprising all relevant coagulation factors and inhibitors at physiological concentrations (minus factor VII when mimicking hemophilia A conditions) and activated platelets (as described. on p. 543 in Monroe et al. (1997) Brit. J. Haematol. 99, 542-547, which is hereby incorporated as reference)

The activity of the Factor VII polypeptides may also be measured using a one-stage clot assay (assay 4) essentially as described in WO 92/15686 or U.S. Pat. No. 5,997,864. Briefly, the sample to be tested is diluted in 50 mM Tris (pH 7.5), 0.1% BSA and 100 µl is incubated with 100 µl of Factor VII deficient plasma and 200 µl of thromboplastin C containing 10 mM $Ca^{2+}$. Clotting times are measured and compared to a standard curve using a reference standard or a pool of citrated normal human plasma in serial dilution.

Preparation and Purification of Factor VII Polypeptides:

Human purified Factor VIIa suitable for use in the present invention is preferably made by DNA recombinant technology, e.g. as described by Hagen et al., Proc. Natl. Acad. Sci. USA 83: 2412-2416, 1986, or as described in European Patent No. 200.421 (ZymoGenetics, Inc.). Factor VII may also be produced by the methods described by Broze and Majerus, J. Biol. Chem. 255 (4): 1242-1247, 1980 and Hedner and Kisiel, J. Clin. Invest. 71: 1836-1841, 1983. These methods yield Factor VII without detectable amounts of other blood coagulation factors. An even further purified Factor VII preparation may be obtained by including an additional gel filtration as the final purification step. Factor VII is then converted into activated factor VIIa by known means, e.g. by several different plasma proteins, such as factor XIIa, IX a or Xa. Alternatively, as described by Bjoern et al. (Research Disclosure, 269 September 1986, pp. 564-565), factor VI may be activated by passing it through an ion-exchange chromatography column, such as Mono Q® (Pharmacia fine Chemicals) or the like, or by autoactivation in solution.

Factor VII-related polypeptides may be produced by modification of wild-type Factor VII or by recombinant technology. Factor VII-related polypeptides with altered amino acid sequence when compared to wild-type Factor VII may be produced by modifying the nucleic acid sequence encoding wild-type factor VII either by altering the amino acid codons or by removal of some of the amino acid codons in the nucleic acid encoding the natural factor VII by known means, e.g. by site-specific mutagenesis.

It will be apparent to those skilled in the art that substitutions can be made outside the regions critical to the function of the factor VIIa molecule and still result in an active polypeptide. Amino acid residues essential to the activity of the Factor VII polypeptide, and therefore preferably not subject to substitution, may be identified according to procedures known in the art, such as site-directed mutagenesis or alanine-scanning mutagenesis (see, e.g., Cunningham and Wells, 1989, Science 244: 1081-1085). In the latter technique, mutations are introduced at every positively charged residue in the molecule, and the resultant mutant molecules are tested for coagulant, respectively cross-linking activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, Science 255: 306-312; Smith et al., 1992, Journal of Molecular Biology 224: 899-904; Wlodaver et al., 1992, FEBS Letters 309: 59-64).

The introduction of a mutation into the nucleic acid sequence to exchange one nucleotide for another nucleotide may be accomplished by site-directed mutagenesis using any of the methods known in the art. Particularly useful is the procedure that utilizes a super coiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI, which is specific for methylated and hemimethylated DNA to digest the parental DNA template and to select for mutation-containing synthesized DNA. Other procedures known in the art for creating, identifying and isolating variants may also be used, such as, for example, gene shuffling or phage display techniques.

Separation of polypeptides from their cell of origin may be achieved by any method known in the art, including, without limitation, removal of cell culture medium containing the desired product from an adherent cell culture; centrifugation or filtration to remove nonadherent cells; and the like.

Optionally, Factor VII polypeptides may be further purified. Purification may be achieved using any method known in the art, including, without limitation, affinity chromatography, such as, e.g., on an anti-Factor VII antibody column (see, e.g., Wakabayashi et al., J. Biol. Chem. 261:11097, 1986; and Thim et al., Biochem. 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J. C. Janson and Lars Ryden, editors, VCH Publishers, New York, 1989. Following purification, the preparation preferably contains less than about 10% by weight, more preferably less than about 5% and most preferably less than about 1%, of non-Factor VII polypeptides derived from the host cell.

Factor VII polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., Biochem. 11:2853 (1972); Thomas, U.S. Pat. No. 4,456,591; and Hedner et al., J. Clin. Invest. 71:1836 (1983). Alternatively, Factor VII polypeptides may be activated by passing it through an ion-exchange chromatography column, such as Mono Q® (Pharmacia) or the like, or by autoactivation in solution. The resulting activated Factor VII polypeptide may then be formulated and administered as described in the present application.

The following examples illustrate practice of the invention. These examples are for illustrative purposes only and are not intended in any way to limit the scope of the invention claimed.

EXPERIMENTAL EXAMPLES

Example 1

Assay Methods

The content of aggregates is determined by non-denaturing size exclusion HPLC. The content of oxidized forms is determined by RP-HPLC. The content of enzymatic degradation forms is determined by RP-HPLC.

Nondenaturing size exclusion chromatography was run on a Waters Protein Pak 300 SW column, 7,5×300 mm using 0.2 M ammoniumsulfat, 5% 2-propanol pH 7,0 as mobile phase. Flow rate: 0.5 ml/min. Detection: 215 nm. Load: 25µg FVIIa.

Reverse phase HPLC was run on a proprietary 4.5×250 mm butylbonded silica column with a particle size of 5µm and pore size 300 Å. Column temperature: 70° C. A-buffer: 0.1% v/v trifluoracetic acid. B-buffer: 0.09% v/v trifluoracetic acid, 80% v/v acetonitrile. The column was eluted with a linear gradient from X to (X+13)% B in 30 minutes. X is adjusted so that FVIIa elutes with a retention time of approximately 26 minutes. Flow rate: 1.0 ml/min. Detection: 214 nm. Load: 25 µg FVIIa.

Example 2

Composition Preparation

In general, aqueous FVIIa composition samples for analysis in these experimental examples were prepared from a purified bulk solution by buffer exchange on a gel filtration column. Composition additives were either contained in the elution buffer in their final ratios or added to the eluate. The resulting solution was sterile filtered using a sterilized membrane filter (0.2 micron pore size or equivalent) and filled into sterile glass vials, stoppered and sealed with butyl rubber stoppers and aluminum flip-off type caps.

Example 3

Effect of pH on the Chemical/Physical Stability

Vials of the rFVIIa aqueous composition containing 1.4 mg rFVIIa/mL, 50 mM Sodium chloride, 10 mM Calcium chloride and a mixture of 10 mM glycylglycine, acetate and histidine adjusted to pH 3, 3.5, 4.0, 4.5, 5.0, 5.5, 6.0, 6.5, 7.0, 7.5, 8.0, 8.5, and 9.0 were incubated at either a temperature of 2-8° C., or at elevated storage temperatures of 30° C., and then removed at various time points and assayed for changes in pH and the chemical stability was determined by RP-HPLC and GP-HPLC.

Figure 1:
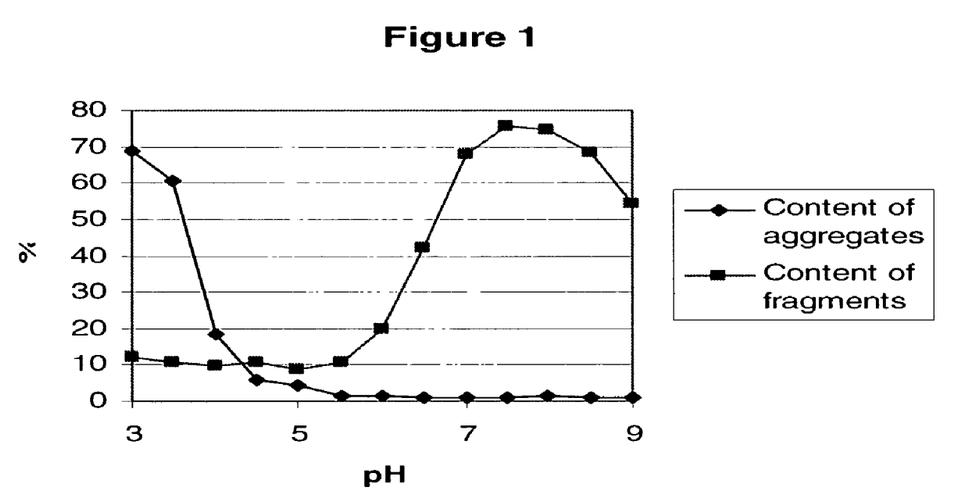
FIG. 1 shows contents of FVII aggregates and FVII fragments after 3 months of storage at 2-8° C.

After storage at 2-8° C. for up to three months the aqueous compositions showed insignificant changes in pH. Non-denaturing size exclusion HPLC performed on samples stored for up to three months at 2-8 ° C. showed no significant aggregation of the drug product at pH values ≧5.5 (FIG. 1). RP-HPLC performed on these samples showed no significant increase in the fragmentation or oxidation of the protein in the pH range 4.5-5.5.

FIG. 1 shows data after 3 months of storage at 2-8 degrees C. The initial content of aggregates is approximately 0.5% and the initial content of fragments is approximately 9%.

Example 4

The Buffer Capacity of Different Buffers

Vials of the rFVIIa aqueous composition containing 1.0 mg rFVIIa/mL, 50 mM Sodium chloride, 10 mM Calcium chloride and one of the following buffer substances in a concentration of 10 mM glycylglycine, malic acid, acetic acid, histidine, glutamic acid and citric acid were incubated at either a temperatures of 2-8.degree. C., or at elevated storage temperatures of 30.degree. C. for up to 3 months. The pH was at time zero adjusted to 5.5 as this gave the least amount of degradation products (FIG. 1). The measurement of the pH in the composition containing glycylglycine showed an increase up to 6.2 in the storage period. The other compositions showed in the same period stable values of 5.5+/−0.1.

Example 5

Physical Stability of Aqueous Compositions Containing Various Detergents

Twelve different compositions were prepared. The compositions were

| | |
|---|---|
| rFVIIa | 0.75 mg/ml |
| NaCl | 2.92 mg/ml |
| CaCl2, 2 H2O | 1.47 mg/ml |
| Glycylglycine | 1.32 mg/ml |
| Detergent/solubiliser | x mg/ml |
| pH | 5.5 |

The concentrations of the detergents/solubilisers tested are stated in the table below.

The compositions were prepared from a liquid bulk solution of rFVIIa. Stock solutions of the detergents/solubilizers were prepared in buffers containing NaCl, CaCl2, 2H2O, and glycylglycine in the concentrations stated above. The rFVIIa bulk and the detergent solutions were mixed, and the pH in the solutions was adjusted to 5.5. The compositions were filtered (0.2 µm) and filled in vials (1 ml solution per vial).

The appearance of the compositions was determined by visual inspection and the absorbance of the composition at 400 nm was determined. Subsequently, the vials were shaken for 19 hours (800/min) at room temperature. After completing the shaking, the appearance and the absorbance at 400 nm was determined. The results are listed in the table below.

| Detergent type | Conc. (mg/ml) | Apperance Before | Apperance After | Absorbance (400 nm) Before | Absorbance (400 nm) After | Absorbance (400 nm) Increase |
|---|---|---|---|---|---|---|
| None (reference) | — | Few part. | Very turbid | 0.0085 | 1.4386 | 1.4301 |
| Tween ® 80 | 0.1 | Very few part. | Clear, few part. | 0.0044 | 0.0036 | 0.0008 |
| Tween ® 20 | 0.1 | Very few part. | Clear, few part. | 0.0039 | 0.0101 | 0.0062 |
| Poloxamer 188 | 1.0 | Very few part. | Clear, few part. | 0.0063 | 0.0027 | 0.0036 |
| Pluronic ® F127 | 1.0 | Very few part. | Clear, few part. | 0.0000 | 0.0048 | 0.0048 |
| Polyethylenglycol 400 | 0.1 | Very few part. | Turbid | 0.0076 | 1.5708 | 1.5632 |
| Polyethylenglycol 4000 | 0.5 | Few part. | Very turbid | 0.0108 | 1.6624 | 1.6516 |
| Bril ® 35 | 0.1 | Very few part. | Clear, few part. | 0.0028 | 0.0015 | 0.0013 |
| Myrj ® 59 | 0.1 | Very few part. | Clear, few part. | 0.0002 | 0.1110 | 0.1108 |
| Myrj ® 52 | 0.1 | Very few part. | Clear, few part. | 0.0009 | 0.9390 | 0.9381 |
| LPCM | 0.1 | Very few part. | Clear, few part. | 0.0026 | 0.0012 | 0.0014 |
| Glycerol | 1.0 | Very few part. | Turbid | 0.0040 | 1.4064 | 1.4024 |

"Part." = "particles"

The results show that the reference (without addition of any detergent/solubilizer) becomes visually turbid when shaken and a significant increase is observed in the absorbance at 400 nm. Addition of Tween® 20 (=polysorbate 20), Tween® 80 (=polysorbate 80), Poloxamer 188, Pluronic® F127 (=poloxamer 407), Brij® 35 (=polyoxyl 23 lauryl ether), and LPCM (=α-lysophasphatidylcholine myristoyl) almost completely prevented increase in turbidy and absorbance, while a slighter increase in turbidity (as compared to the reference) was observed for Myrj® 59 (=polyoxyl 100 stearate) and Myrj® 52 (=polyoxyl 40 stearate). Glycerol, polyethylene glycol 400 or polyethylene glycol 4000 could not prevent increase in turbidity in the concentrations used in this experiment.

Example 6

Chemical Stability of Aqueous Compositions Containing Methionine as Antioxidant

Three different compositions were prepared. The compositions were:

| | |
|---|---|
| rFVIIa | 0.75 mg/ml |
| NaCl | 2.92 mg/ml |
| CaCl2, 2 H2O | 1.47 mg/ml |
| Glycylglycine | 1.32 mg/ml |
| Methionine | 0 or 0.25 or 1.0 mg/ml |
| pH | 6.5 |

The compositions were prepared from a liquid bulk solution of rFVIIa. The methionine was dissolved in buffers containing NaCl, CaCl$_2$, 2H$_2$O, and glycylglycine in the concentrations stated above. The rFVIIa bulk and the methionine solutions were mixed, and the pH in the solutions was adjusted to 6.5. The compositions were filtered (0.2 μm) and filled in vials (1 ml solution per vial). The vials were stored at 5° C., 25° C. and 40° C. Samples were withdrawn and analyzed for content of oxidized forms (by RP-HPLC) at the time point stated in the table below. The table shows the content of oxidized forms (in %).

| Methionine (mg/ml) | Time zero | 25° C. 14 days | 40° C. 14 days | 25° C. 28 days | 40° C. 28 days | 5° C. 90 days |
|---|---|---|---|---|---|---|
| 0 (reference) | 2.4 | 4.4 | 7.5 | 4.4 | 12.8 | 3.1 |
| 0.25 | 1.7 | 2.4 | 5.3 | 2.8 | 9.9 | 1.9 |
| 1.0 | 1.6 | 2.3 | 5.0 | 2.6 | 9.6 | 1.3 |

The results show that addition of methionine slows down the oxidation rate in the composition.

Example 7

Chemical Stability of Aqueous Compositions Containing Calcium Chloride

Four different compositions were prepared. The compositions were:

| | |
|---|---|
| rFVIIa | 1.0 mg/ml |
| NaCl | 2.92 mg/ml |
| CaCl2, 2 H2O | 1.47 mg/ml (10 mM), 29.4 mg/mL (200 mM), 58.8 mg/mL (400 mM) and 117.6 mg/mL (800 mM), respectively |
| Glycylglycine | 1.32 mg/ml |
| pH | 7.0 |

The compositions were prepared from a liquid bulk solution of rFVIIa. Calcium chloride was dissolved in buffers containing NaCl and glycylglycine to give the concentrations stated above after mixing with rFVIIa bulk. After mixing the pH in the solutions was adjusted to 7.0. The compositions were filtered (0.2 μm) and filled in vials (1 ml solution per vial). The vials were stored at 5° C.

The activity of factor VII (IU/ml) was determined by clot assay.

| Composition Content of Calcium chloride | 0 mdr IU/ml | 3 mdr IU/ml 5° C. |
|---|---|---|
| 1 (10 mM) | 54444 | 33623 |
| 2 (200 mM) | 59917 | 46528 |
| 3 (400 mM) | 54680 | 59370 |
| 4 (800 mM) | 51773 | 52801 |

Heavy Chain Degradation

The formation of heavy chain fragments was measured by RP-HPLC as described in example 1 during storage of the formulations. The results (% fragments) are shown in the table below.

| For-mulation | 0 month | 1 month 30° C. | 1 month 5° C. | 2 months 5° C. | 3 months 5° C. | 6 months 5° C. |
|---|---|---|---|---|---|---|
| 1 (10 mM) | 9.4 | 27.9 | 31.7 | 52.5 | 52.5 | 65.6 |
| 2 (200 mM) | 7.9 | 14.7 | 15.6 | 27.1 | 27.1 | 38.5 |
| 3 (400 mM) | 7.3 | 11.2 | 10.9 | 16.9 | 16.9 | 23.2 |
| 4 (800 mM) | 7.4 | 8.3 | 8.0 | 9.2 | 9.2 | 10.5 |

Example 8

Chemical Stability of Aqueous Solutions Containing Magnesium

Six formulations containing varied contents of CaCl2, MgSO4, or MgCl2 (see the table below) were prepared. CaCl2 in the purified bulk solution was removed using chelex and the formulations were then prepared by addition of stock solutions containing the excipients.

| Formulation | Salt concentration |
|---|---|
| 1 | 200 mM $CaCl_2$ |
| 2 | 400 mM $CaCl_2$ |
| 3 | 200 mM $MgSO_4$ + 2 mM $Ca^{2+}$ |
| 4 | 400 mM $MgSO_4$ + 2 mM $Ca^{2+}$ |
| 5 | 200 mM $MgCl_2$ + 2 mM $Ca^{2+}$ |
| 6 | 400 mM $MgCl_2$ + 2 mM $Ca^{2+}$ |

In addition to the salts stated above, all formulations contained 1.0 mg/ml rFVIIa, 20 mM glycylglycine, 20 mM L-histidine, and 50 mM NaCl. The pH was adjusted to pH 7.0. The formulations were sterile filtered, filled into cartridges and stored at 5° C. During storage the content of heavy chain fragments were measured by RP-HPLC. The results (as % fragments) shown in the table below were obtained.

| Formulation | Months at 5° C. | | | |
|---|---|---|---|---|
| | 0 | 1 | 2 | 3 |
| 1 | 8.8 | 16.9 | 25.2 | 29.8 |
| 2 | 8.4 | 11.3 | 15.1 | 18.0 |
| 3 | 9.1 | 17.1 | 25.6 | 29.8 |
| 4 | 8.6 | 12.7 | 16.9 | 19.7 |
| 5 | 9.8 | 22.6 | 33.0 | 38.6 |
| 6 | 9.8 | 22.1 | 32.4 | 37.5 |

Example 9

Effect of Ionic Strength on Chemical Stability

Four formulations were prepared by mixing purified rFVIIa bulk solution with stock solutions containing excipients. In the formulations the contents of NaCl and CaCl2 were varied as shown in the table below

| Formulation | mg/mL NaCl | mg/mL $CaCl_2$ |
|---|---|---|
| A | 2.92 | 1.47 |
| B | 58.4 | 1.47 |
| C | 2.92 | 7.35 |
| D | 58.4 | 7.35 |

Furthermore, all formulations contained 1 mg/ml rFVIIa, 10 mM Glycylglycine, 10 mM Sodium acetate, and 10 mM L-Histidine. The pH was adjusted to 7.0 in all formulations.

The formulations were stored at 30° C. and the contents of heavy chain fragments were measured by RP-HPLC (example 1). The results (as % fragments) are listed in the table below.

| Formulation | 0 month | 1 months | 2 months | 3 months |
|---|---|---|---|---|
| A | 12.7 | 31.3 | 39.1 | 43.6 |
| B | 9.8 | 19.1 | 23.2 | 26.7 |
| C | 11.1 | 24.0 | 29.9 | 33.6 |
| D | 9.8 | 20.2 | 25.3 | 28.6 |

The results show that a higher ionic strength (here obtained by addition of either NaCl or CaCl2) results in a decreased formation of heavy chain fragments during storage.

The invention claimed is:

1. A liquid, aqueous composition comprising:
   (i) a factor VII polypeptide;
   (ii) an agent suitable for keeping pH in the range of from about 5.5 to about 7.0;
   (iii) a calcium salt in a concentration of at least 200 mM, such that the composition is hypertonic;
   wherein said composition has decreased formation of heavy chain fragments upon storage of said aqueous composition for 6 months at 2-8° C. as compared with non-hypertonic compositions and wherein said factor VII polypeptide retains at least 50% of its initial biological activity.

2. A composition according to claim 1, further comprising (iv) an ionic strength modifying agent.

3. A composition according to claim 2, wherein the ionic strength modifying agent (iv) is selected from the list of: a neutral salt, e.g., sodium chloride; an amino acid; or a small peptide, or a mixture of at least two of said modifying agents.

4. A composition according to claim 3, wherein the ionic strength modifying agent (iv) is sodium chloride.

5. A composition according to claim 2, wherein the agent (iv) is present in a concentration of at least about 5 mM.

6. A composition according to claim 1, wherein the calcium salt is selected from the group consisting of calcium chloride, calcium acetate, calcium gluconate, and calcium laevulate.

7. A composition according to claim 1, wherein the tonicity modifying agent (v) is selected from the group consisting of: a neutral salt; a monosaccharide; a disaccharide; polysaccharide; a sugar alcohol; an amino acid; a peptide, and a mixture of at least two of said modifying agents.

8. A composition according to claim 1, further comprising (vi) a non-ionic surfactant.

9. A composition according to claim 8, wherein the non-ionic surfactant is a polysorbate or a poloxamer or a polyoxyethylene alkyl ether.

10. A composition according to claim 1, further comprising (vii) an antioxidant.

11. A composition according to claim 10, wherein the antioxidant (vii) is selected from the group consisting of: L- or D-methionine, ascorbic acid, cysteine, homocysteine, gluthatione, cystine, and cysstathionine.

12. A composition according to claim 11, wherein the antioxidant is L-methionine.

13. A composition according to claim 10, wherein the antioxidant is present in a concentration of from about 0.1 to about 5.0 mg/ml.

14. A composition according to claim 1, wherein the agent suitable for keeping pH in the range of from about 5.5 to about 7.0 is selected from the group consisting of acids and salts of citrate, acetate, histidine, malate, phosphate, tartaric acid, succinic acid, MES, HEPES, Imidazol, TRIS, lactate, glycylglycin, PIPES, glycin, and a mixture of at least two of said agents.

15. A composition according to claim 14, wherein the concentration of the agent is from about 1 mM to about 50 mM.

16. A composition according to claim 15, wherein the concentration of the agent is about 10 mM.

17. A composition according to claim 1, further comprising (viii) a preservative selected from the group consisting of phenol, benzyl alcohol, orto-cresol, meta-cresol, para-cresol, methyl paraben, propyl paraben, benzalconium chloride, and benzaethonium chloride.

18. A composition according to claim 1, wherein said factor VII polypeptide is stable for at least 6 months at 2-8° C.

19. A composition according to claim 1, wherein the factor VII polypeptide is recombinantly made human factor VIIa.

20. A composition according to claim 1, wherein the factor VII polypeptide is present in a concentration of from about 0.1 mg/ml to about 10 mg/ml.

21. A method for preparing a liquid, aqueous composition of a factor VII polypeptide, comprising the step of providing the factor VII polypeptide in a solution comprising (ii) an agent suitable for keeping pH in the range of from about 5.5 to about 7.0; (iii) a calcium salt in a concentration of at least 200 mM, such that the composition is hypertonic; wherein composition retains at least 50% of its initial biological activity upon storage of said aqueous composition for 6 months at 2-8° C.

22. A method for treating a factor VII-responsive syndrome, the method comprising administering to a subject in need thereof an effective amount of an aqueous liquid composition comprising (i) a factor VII polypeptide, (ii) an agent suitable for keeping pH in the range of from about 5.5 to about 7.0; (iii) a calcium salt in a concentration of at least 200 mM, such that the composition is hypertonic; wherein said composition retains at least 50% of its initial biological activity upon storage of said aqueous composition for 6 months at 2-8° C., and wherein said factor VII-responsive syndrome is selected from the group consisting of: haemophilia A, haemophilia B, Factor Xi deficiency, Factor VII deficiency, thrombocytopenia, von Willebrand's disease, presence of a clotting factor inhibitor, surgery, intra cerebral haemorrhage, trauma, and anticoagulant therapy.

* * * * *